(12) United States Patent  
Maschke

(10) Patent No.: US 8,534,916 B2  
(45) Date of Patent: Sep. 17, 2013

(54) APPARATUS WITH TWO PAIRS COMPRISING X-RAY SOURCE AND X-RAY DETECTOR

(75) Inventor: Michael Maschke, Lonnerstadt (DE)

(73) Assignee: Siemens Aktiengesellshaft, München (DE)

( * ) Notice: Subject to any disclaimer, the term of this patent is extended or adjusted under 35 U.S.C. 154(b) by 332 days.

(21) Appl. No.: 13/103,268

(22) Filed: May 9, 2011

(65) Prior Publication Data

US 2011/0274247 A1    Nov. 10, 2011

(30) Foreign Application Priority Data

May 10, 2010   (DE) .......................... 10 2010 019 989

(51) Int. Cl.  
*H05G 1/02* (2006.01)

(52) U.S. Cl.  
USPC ......................................................... 378/197

(58) Field of Classification Search  
USPC ... 378/9, 19, 62, 98.8, 193–198; 250/370.08, 250/370.09, 370.11  
See application file for complete search history.

(56) References Cited

U.S. PATENT DOCUMENTS

| | | | |
|---|---|---|---|
| 7,020,235 B2 | 3/2006 | Hornegger et al. | |
| 7,263,157 B2 | 8/2007 | Bruder et al. | |
| 7,359,484 B2 | 4/2008 | Qui et al. | |
| 7,594,751 B2 * | 9/2009 | Grebner et al. | 378/197 |
| 2006/0120507 A1 | 6/2006 | Brunner et al. | |

FOREIGN PATENT DOCUMENTS

| | | |
|---|---|---|
| DE | 102 41 184 A1 | 4/2004 |
| DE | 198 02 405 B4 | 7/2004 |
| DE | 10 2007 049 298 A1 | 4/2008 |
| DE | 10 2008 016 891 A1 | 10/2009 |
| DE | 10 2008 019 646 A1 | 10/2009 |

OTHER PUBLICATIONS

Siemens AG, Healthcare Sector, Artis zee, "Advanced applications in interventional radiology", www.siemens.com/healthcare, Order No. A91AX-20822-12C1-766, Printed in Germany © Jan. 2009 Siemens AG, pp. 1-14, Others 2009.
Siemens AG, Medical Solutions, Arta zee, "Ceiling-mounted system for surgical angiography", Data sheet , www.siemens.com/healthcare, Order No. A91AX-20805-31T1-7600, Printed in Germany, pp. 128, Others, Aug. 2008.

* cited by examiner

*Primary Examiner* — Courtney Thomas

(57) ABSTRACT

An apparatus with two pairs of X-ray systems is provided. Each of the X-ray systems has an X-ray source and an X-ray detector. The X-ray detectors differ from each other in their spatial resolution. The X-ray detector with the low spatial resolution makes it possible to record X-ray images in a faster temporal sequence than the other. The doctor carrying out the treatment thus has the option of deciding between the availability of a high spatial resolution and the recording of images in a rapid temporal sequence.

9 Claims, 1 Drawing Sheet

APPARATUS WITH TWO PAIRS COMPRISING X-RAY SOURCE AND X-RAY DETECTOR

CROSS REFERENCE TO RELATED APPLICATIONS

This application claims priority of German application No. 10 2010 019 989.3 filed May 10, 2010, which is incorporated by reference herein in its entirety.

FIELD OF THE INVENTION

The invention relates to an apparatus with a first pair comprising a first X-ray source and a first X-ray detector and a second pair comprising a second X-ray source and a second X-ray detector.

BACKGROUND OF THE INVENTION

Such apparatuses are known in their conventional form of embodiment as a biplane X-ray system. Each pair of X-ray source and X-ray detector can record X-ray images. The pairs are arranged such that an image of the same object is able to be recorded by both pairs, especially simultaneously. The object is typically located on a patient table which is located in the beam path from the X-ray source to the X-ray detector for both pairs, or this state is at least able to be established, be it by a movement of the patient table or be it by a movement of the X-ray source and X-ray detector.

Under normal circumstances there are means to move the X-ray source and the X-ray detector, i.e. to bring the same into specific positions. Typically a pair comprising X-ray source and X-ray detector are coupled and moved together, however the present invention is also able to be used if the X-ray source and the X-ray detector of a pair are able to be moved independently of one another.

In a biplane X-ray system from the applicant's own company Siemens AG for example, an X-ray C-arm is suspended from the ceiling of a room, a second arm is coupled to a floor mount.

The advantage of simply providing two pairs of X-ray source and X-ray detector is that of enabling the presentation to be switched very rapidly: A doctor carrying out the treatment can X-ray a patient with the aid of the first pair of X-ray source and X-ray detector from a prespecified perspective and can then switch the perspective very rapidly by using the second pair of X-ray source and X-ray detector. It is known from DE 102 41 184 A1 that a volume dataset of an object is able to be calculated from the X-ray images (2D projections) obtained by the two pairs of X-ray source and X-ray detector, especially synchronously.

In a hospital environment it is a matter of utilizing available devices in the optimum possible manner. It is therefore advantageous for them to be versatile in their uses.

Said biplane X-ray systems are used in particular to support imaging in minimally-invasive interventions and surgical procedures on patients. In such procedures it is of importance for the doctor carrying out the treatment to obtain images, of soft tissue for example; these can be useful for procedures on the heart and liver. A flat-panel X-ray detector with a good local resolution is thus required. For example such a flat-panel detector has detector elements of the size of around 100 µm. Such a detector can be constructed from amorphous Silicon or with the aid of CMOS technology. Future developments are designed to manufacture such flat-panel detectors from Cadmium-Telluride (CdTe) or Cadmium-Zinc-Telluride, or on the basis of organic photodiodes. Such flat-panel detectors are especially usually used in their amorphous silicon versions in X-ray angiography systems.

For recording images of the heart with the aid of computed tomography quite different types of detector are used, namely such as can record images with high frequencies, in order to record the heart multiple times during a heart cycle. These types of computed tomography detectors typically consist of UFC (ultra-fast-ceramic), or they are based on Yttrium-Gadolinium-Oxide, in future also on Cadmium-Telluride (CDTE) or on Cadmium-Zinc-Telluride. Such detectors optimized for a high temporal resolution have the disadvantage of their detector elements having the size of around 400 µm, so that they only offer a limited local resolution.

In the prior art the doctor performing the treatment thus has to decide before an intervention which type of imaging is more important for him, either that with high spatial resolution or that with a faster temporal sequence of image recording; he must then treat his patient at a specific device. In addition the two types of device are not always available in a hospital environment.

SUMMARY OF THE INVENTION

The object of the invention is thus to increase flexibility in diagnostic imaging for the doctor carrying out the treatment.

The object is achieved by an apparatus with the features in accordance with the claims.

Inventively, in the apparatus with two pairs comprising X-ray source and X-ray detector, the first X-ray detector provides images in a better spatial resolution than the second X-ray detector, while the second X-ray detector is designed to provide images in a more rapid temporal sequence than the first X-ray detector.

The doctor carrying out the treatment can thus place the patient in or on the inventive apparatus and then decide at short notice whether he wishes to have images with a good spatial resolution or images in a rapid temporal sequence, or whether he wishes to switch within a short space of time from one to the other. If necessary it is even possible for the doctor to operate both pairs comprising X-ray source and X-ray detector simultaneously and thus simultaneously obtain on the one hand images of the patient with high spatial resolution and on the other hand obtain images captured within a rapid temporal sequence.

The first X-ray detector is preferably an X-ray detector such as is used in conventional X-ray angiography systems as a flat-panel detector and is made of the materials described above for a flat panel X-ray detector.

The second X-ray detector is preferably a detector such as is manufactured in computed tomography devices and it consists for example of the materials described above for computed tomography detectors.

In a manner known per se, in at least one of the pairs, the X-ray source and the X-ray detector are preferably arranged on a rotatable X-ray C-arm. These can typically be supported on a floor mount. It is possible for there to be a second X-ray C-arm which carries the second X-ray source and the second X-ray detector. The second X-ray C-arm can then especially be suspended from the ceiling. It can be rotatable but does not necessarily have to be rotatable.

As an alternative to suspension from a room ceiling or to mounting on a room floor, articulated-arm robots can be used, especially those which exhibit at least four, preferably five and especially preferably six degrees of freedom in their movement; typically each degree of freedom corresponds to one axis of rotation. Such articulated-arm robots make it possible to bring the pairs comprising X-ray source and X-ray detector into a plurality of positions, especially relative to a patient support device, so that a plurality of possible perspectives is provided in the image. The use of an articulated-arm robot can be accompanied by the simultaneous use of an X-ray C-arm, by the X-ray C-arm simply being provided as an outlier of the articulated-arm robot. An X-ray C-arm makes especially precise rotations possible. The articulated-arm robot can stand on the floor or be suspended from a wall or from the ceiling of the room.

Instead of an X-ray C-arm, U-arms can also be used or sources and detectors can be attached to individual supports in each case.

As an alternative the second source-detector combination can be arranged in a ring.

In the form of embodiment with two X-ray C-arms it is preferred for both X-ray C-arms to be of the same size. This form of embodiment has the advantage that the two pairs comprising X-ray source and X-ray detector are to a certain extent of equal importance and similar images can be created by them at least from the projection geometry standpoint. This applies both when the X-ray C-arms are suspended from the ceiling or stand directly on a mount on the floor or when they are provided as outliers of an articulated-arm robot which then stands on the floor or is suspended from the ceiling.

In the form of embodiment with two X-ray C-arms it is especially advantageous for these to be supported rotatably on a common joint. The common joint can be a ball joint for example.

The use of a common joint means that the rotation orientations of the two X-ray C-arms are comparable, especially when the two X-ray C-arms are also of the same size. This makes it possible to better assign the respective images obtained to each other.

The measure of having the X-ray C-arms equal in size and/or rotatably supported on a common joint especially makes possible in one form of embodiment the realization of an advantageous development of the invention, in accordance with which the apparatus has a patient support device available to it, with the relative positions of X-ray source and X-ray detector in relation to the patient support device able to be defined and wherein a special feature consists of at least some of these relative positions being able to be recorded both by the first pair of X-ray source and X-ray detector and also by the second pair of X-ray source and X-ray detector.

This property which is not absolutely necessary with conventional biplane X-ray systems is above all advantageous because different types of image are able to be recorded by the different pairs of X-ray source and X-ray detector. It can then be that the doctor carrying out the treatment would like to obtain both types of image from a specific imaging perspective. If for example he has first observed a specific region of interest of a patient with high spatial resolution, it can be that he subsequently requires a good temporal resolution, but that he then requires these images obtained with the high temporal resolution to be able to be compared with the image with high spatial resolution. In these cases it is advantageous for the second X-ray source to be able to be placed precisely where the first X-ray source was previously placed and for the second X-ray detector to be placed where the first X-ray detector was initially placed. Basically the position of X-ray source and X-ray detector can also be swapped.

Said preferred forms of embodiment with the same size of X-ray C-arm on a common joint have the advantage that at least in the embodiment in accordance with this form of embodiment just described, the respective positions of the one X-ray C-arm can be especially easily reproduced by the other X-ray C-arm.

In any event at least one additional degree of freedom can be obtained by a movement of the patient table: The patient table can be floor-mounted, wall-mounted or ceiling-mounted and preferably able to be adjusted in its height or its longitudinal and transverse direction manually or by a motor, if necessary it can also be tilted or rotated around a central point or can execute circular or elliptical rotational movements around a fixed point in the plane or the room. The X-ray source can be embodied as an emitter which comprises carbon nanotubes in accordance with U.S. Pat. No. 7,359,484 B2.

BRIEF DESCRIPTION OF THE DRAWINGS

While the invention as such is able to be realized with any given mechanical constructions, two preferred embodiments of the inventive apparatus will be described below, with reference to the drawing, in which.

DETAILED DESCRIPTION OF THE INVENTION

Figure 1:
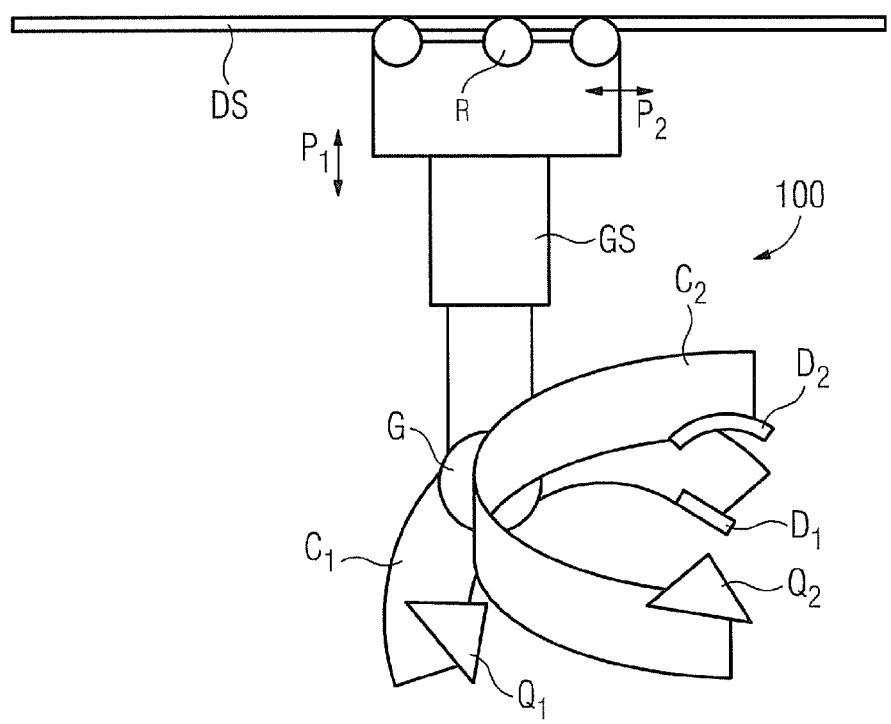
FIG. 1 shows a basic diagram of an inventive apparatus in accordance with a first form of embodiment of the invention and FIG. 2 shows a perspective view with part of the basic diagram of a second form of embodiment of an inventive apparatus.
Figure 2:
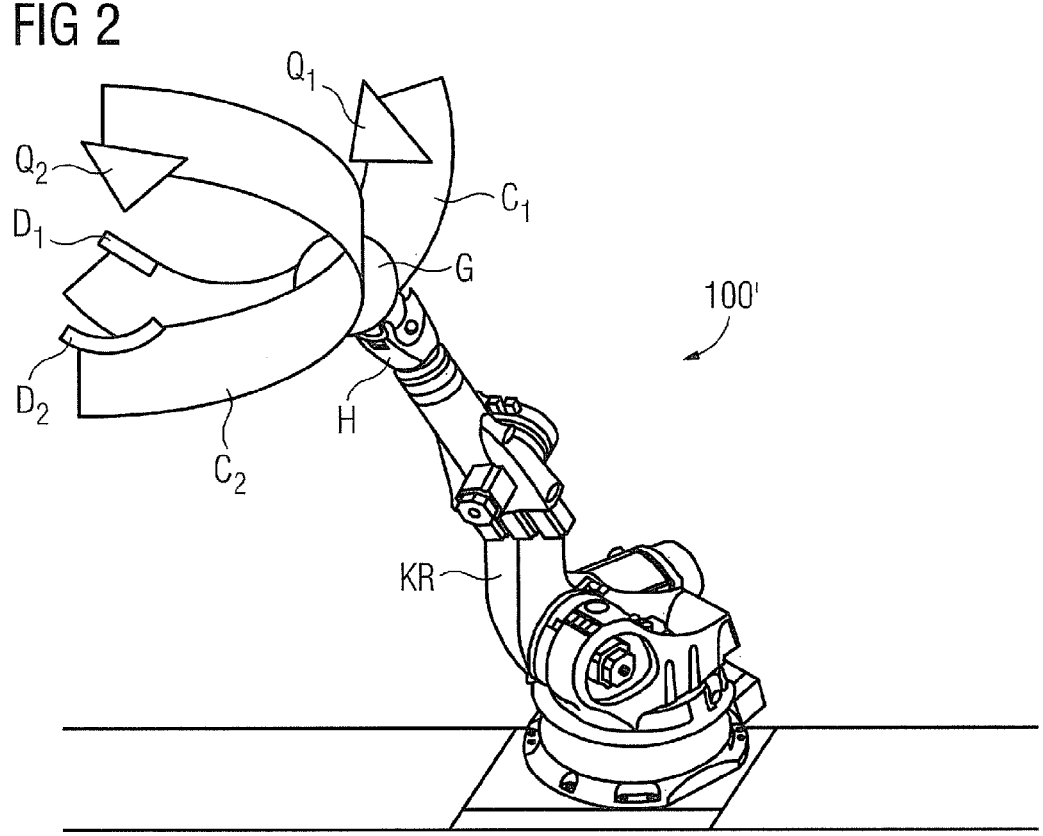

The common factor in the two forms of embodiment in accordance with FIG. 1 and FIG. 2 is that a respective apparatus 100, 100' features two X-ray $C_1$ and $C_2$, which each bear an X-ray source $Q_1$, $Q_2$ and an X-ray detector $D_1$, $D_2$.

In this invention the two detectors $D_1$, $D_2$ differ in their construction: the first X-ray detector $D_1$ should be a known flat-panel detector from conventional X-ray angiography systems, as based for example on amorphous silicon or CMOS. The second X-ray detector $D_2$ should be a detector conventionally used in computed tomography systems, e.g. an Ultrafast-Ceramic-Detector (UFC), a detector based on Yttrium-Gadolinium-Oxide, or a detector based on Cadmium-Telluride or Cadmium-Zinc-Telluride.

The first X-ray detector $D_1$ has a high local resolution of 50-150 μm. The second X-ray detector has a lower resolution of only around 300 to 500 μm (400 μm preferably), but is between three times and six times (preferably four times) as fast in recording X-ray images, e.g. up to 120 X-ray images per second can be recorded.

In the apparatus 100 in accordance with the first form of embodiment the two X-ray C-arms $C_1$ and $C_2$ are suspended on a common joint G which is suspended from a strut GS able to be moved transversely in accordance with the arrow $P_1$, which for its part is able to be moved in its entirety on rollers R on a ceiling rail DS in accordance with arrow $P_2$.

The apparatus 100' in accordance with the second form of embodiment also has a common joint G provided which is supported on a hand H of an articulated-arm robot KR with six degrees of freedom (six axes of rotation) as is known per se from the prior art.

Both in the apparatus 100 and also with the apparatus 100' the X-ray C-arms of the same size and because of their suspension on a common joint G can each be brought into precisely the same positions: For example the X-ray C-arm $C_1$ can be brought into a first position and subsequently be moved out of this position again and X-ray C-arm $C_2$ can be moved into the same position. The apparatuses 100 and 100' are able to be used as follows: If the doctor carrying out the treatment would like to have X-ray images with high local resolution available, images are recorded with the pair comprising X-ray source $Q_1$ and X-ray detector $D_1$, especially the so-called 2D projections, with three-dimensional information able to be obtained from a plurality of such images.

If on the other hand the doctor carrying out the treatment needs a good temporal resolution, the pair comprising X-ray source $Q_2$ and X-ray detector $D_2$ are used and in this case two projections can be obtained or 3D reconstructions obtained based on a plurality of projections. Thus images of rapidly moving organs or organ elements can be recorded by this pair for example.

It is possible for the doctor to initially take a plurality of images of a rapidly moving organ in order to obtain an overview and subsequently to look at a specific region of the body or of the organ at a better local resolution. Exactly conversely it is possible for the doctor performing the treatment to first view specific regions of the body or of the organ at an especially good local resolution and then to require a representation with high temporal resolution.

Apparatuses 100 and 100' thus make it possible for the doctor carrying out the treatment to obtain images in an especially flexible manner, depending on the given requirements. The patient in this case is located on a patient table which can be moved or adjusted if necessary (not shown) or there is a facility for supporting just one part of the body of the patient. There need only be one such patient support device on which the patient or a part of the patient's body can remain supported, and this can be done for a specific period of time such as results for example from a minimally-invasive or surgical procedure and during this procedure images can be obtained with two different measures (high local resolution, rapid sequence of images).

The invention claimed is:

1. An apparatus for acquiring an X-ray image, comprising:
 a first pair comprising a first X-ray source and a first X-ray detector; and
 a second pair comprising a second X-ray source and a second X-ray detector,
 wherein the first X-ray detector is configured to provide the X-ray image at a higher resolution than the second X-ray detector, and
 wherein the second X-ray detector is configured to provide the X-ray image in a more rapid temporal sequence than the first X-ray detector.

2. The apparatus as claimed in claim 1, wherein the first X-ray source and the first X-ray detector or the second X-ray source and the second X-ray detector are arranged on an outlier of an articulated-aim robot.

3. The apparatus as claimed in claim 2, wherein the articulated-aim robot comprises four, five, or six degrees of movement freedom.

4. The apparatus as claimed in claim 1,
 wherein the first X-ray source and the first X-ray detector are arranged on a first rotatable X-ray C-arm, and
 wherein the second X-ray source and the second X-ray detector are arranged on a second rotatable X-ray C-arm.

5. The apparatus as claimed in claim 4, wherein the first or the second C-arm is provided as an outlier.

6. The apparatus as claimed in claim 4, wherein the first and the second C-arms are same size.

7. The apparatus as claimed in claim 4, wherein the first and the second C-arms are rotatably supported on a common joint.

8. The apparatus as claimed in claim 1, further comprising a patient support device for supporting a patient to be X-rayed by the first pair and the second pair.

9. The apparatus as claimed in claim 8, wherein positions of the patient support device in relation to positions of the first X-ray source and the first X-ray detector and positions of the second X-ray sources and the second X-ray detector are defined.

\* \* \* \* \*